(12) United States Patent
Slaikeu et al.

(10) Patent No.: US 6,663,607 B2
(45) Date of Patent: *Dec. 16, 2003

(54) BIOACTIVE ANEURYSM CLOSURE DEVICE ASSEMBLY AND KIT

(75) Inventors: Paul C. Slaikeu, Hayward, CA (US); Michael P. Wallace, Pleasanton, CA (US); Joseph C. Eder, Los Altos Hills, CA (US); James J. Barry, Marlborough, MA (US); Robert M. Abrams, Sunnyvale, CA (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/352,187

(22) Filed: Jul. 12, 1999

(65) Prior Publication Data

US 2001/0047202 A1 Nov. 29, 2001

(51) Int. Cl.[7] .................................................. A61M 25/00
(52) U.S. Cl. ........................... 604/265; 604/104; 606/32
(58) Field of Search ....................... 604/265, 104–109, 604/56, 60; 623/1.11, 1.12, 1.15, 1.2, 1.21, 1.22, 1.42, 1.43, 1.44, 1.45, 1.46, 1.48; 128/831, 839, 840; 606/32, 108, 194

(56) References Cited

U.S. PATENT DOCUMENTS

| 3,174,851 A | 3/1965 | Buehler et al. |
| 3,351,463 A | 11/1967 | Rozner et al. |
| 3,753,700 A | 8/1973 | Harrison et al. |
| 4,577,631 A | 3/1986 | Kreamer |
| 4,739,768 A | 4/1988 | Engelson |
| 4,986,831 A | 1/1991 | King et al. |
| 4,994,069 A | 2/1991 | Richart et al. |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,304,194 A | 4/1994 | Chee et al. |
| 5,354,295 A | 10/1994 | Guglielmi et al. |
| 5,382,259 A | 1/1995 | Phelps et al. |
| 5,413,598 A | 5/1995 | Moreland |
| 5,464,449 A | 11/1995 | Ryan et al. |
| 5,609,628 A | 3/1997 | Keranen |

(List continued on next page.)

FOREIGN PATENT DOCUMENTS

| DE | 197 13 213 A1 | 10/1998 |
| EP | 0 547 530 B1 | 9/1996 |
| EP | 0 815 806 A2 | 1/1998 |
| EP | 0 820 726 A2 | 1/1998 |
| WO | WO95/17859 | 6/1995 |
| WO | WO/26939 | 7/1997 |
| WO | WO97/31672 | 9/1997 |
| WO | WO 99/02092 A1 | 1/1999 |
| WO | WO 99/05977 A1 | 2/1999 |

Primary Examiner—Long V. Le
Assistant Examiner—Ann Y Lam
(74) Attorney, Agent, or Firm—Binham McCutchen LLP

(57) ABSTRACT

This is an implantable medical device assembly for use in surgical procedures. It is most preferably an implantable structure having stenting properties but only partially coated with or partially associated with a material causing a localized angiogenic response. One variation of is an artificial occlusion kit having the inventive implantable stenting structure situatable and vaso-occlusive devices. The implantable stenting structure is typically situated so to prevent migration of artificial occlusion devices or implants from an occlusion site, such as an aneurysm, and into an adjacent body space, such as a blood vessel.

30 Claims, 4 Drawing Sheets

U.S. PATENT DOCUMENTS 5,670,161 A * 9/1997 Healy et al. ................. 424/426
5,676,685 A * 10/1997 Razavi ........................ 606/194
5,718,711 A     2/1998 Berenstein et al.
5,853,418 A    12/1998 Ken et al.
5,891,192 A *  4/1999 Murayama et al. ............ 623/1
5,951,599 A     9/1999 McCrory
5,980,514 A * 11/1999 Kupiecki et al. .............. 606/32
6,143,022 A * 11/2000 Shull et al. ................. 623/1.13

* cited by examiner

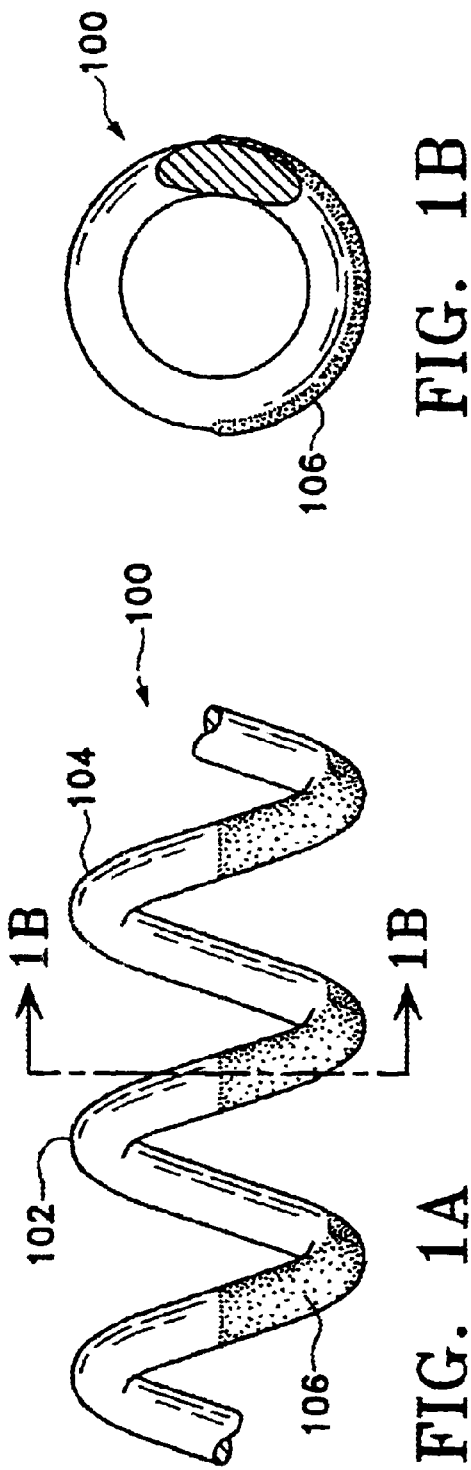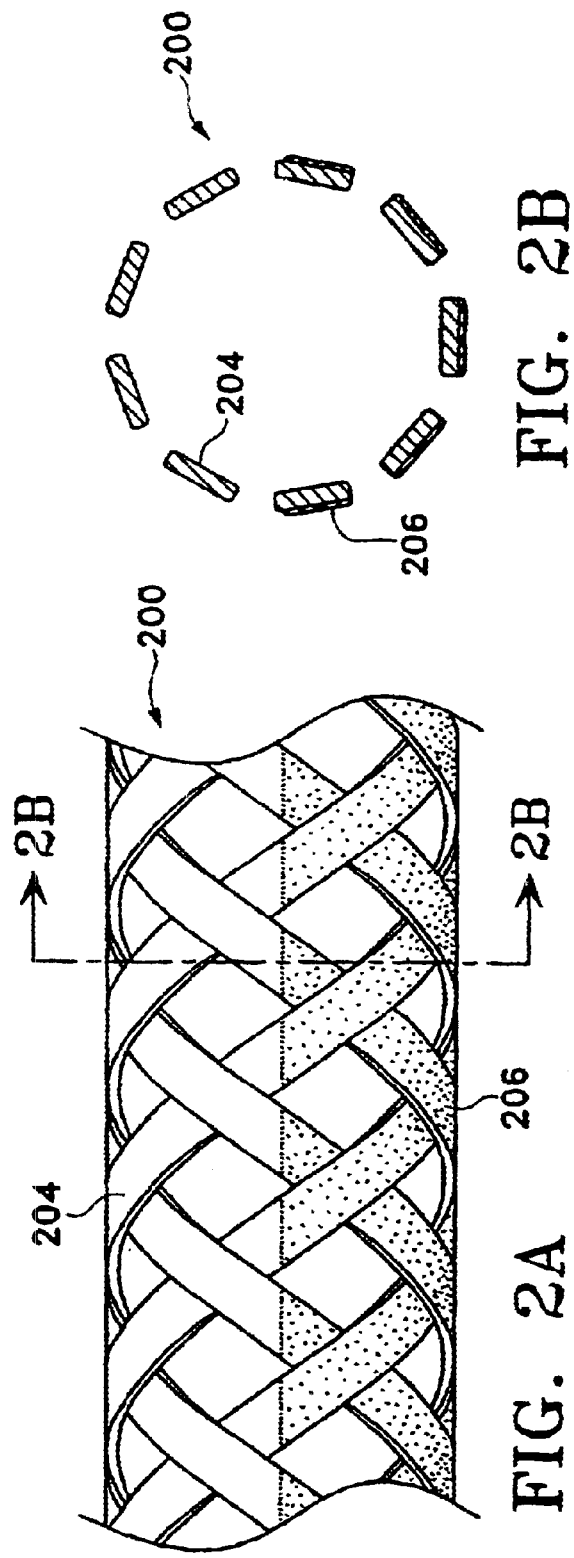

BIOACTIVE ANEURYSM CLOSURE DEVICE ASSEMBLY AND KIT

FIELD OF THE INVENTION

This invention is an implantable medical device assembly for use in surgical procedures. It is most preferably an implantable structure having stenting properties but only partially coated with or partially associated with a material causing an angiogenic response. One variation of the invention is an artificial occlusion kit having the inventive implantable stenting structure situatable and vaso-occlusive devices. The inventive implantable stenting structure is typically situated so to prevent migration of artificial occlusion devices or implants from an occlusion site, such as an aneurysm, and into an adjacent body space, such as a blood vessel.

BACKGROUND OF THE INVENTION

Different implantable medical devices have been developed for treating various ailments associated with body lumens, such as ailments of body vessel walls or other lumenal walls. One category of implantable medical device that has been developed for artificial occlusion of body spaces is the category of "artificial occlusion devices." Although artificial occlusion devices are useful in occluding body spaces, other applications include the occlusion of body lumens. Examples of lumens that have been identified as candidates for treatment with artificial occlusion devices include, for example, the vas deferens or the fallopian tubes. Most commonly, however, artificial occlusion devices have been disclosed for medical treatment of the vascular lumens and aneurysms in the walls of such vessels. This treatment is commonly referred to as "artificial vaso-occlusion."

Artificial Vaso-Occlusion

Artificial vaso-occlusion is a medical treatment that has involved techniques such as the delivery of various occlusive agents including solidifying suspensions, thrombogenic fluids, soublized polymeric compositions, or emboli such as hog hair or suspensions of metal particles. Delivery of such agents or emboli normally causes a thrombogenic or other occlusive tissue response. Recent advancements in artificial occlusion of vessels and aneurysms have included the delivery and implantation of metal coils. Implantable metal coils that are useful as artificial occlusion devices in vascular lumens or aneurysms are herein referred to as "vaso-occlusion coils."

Vaso-occlusion coils generally are constructed of a wire, usually made of a coils may be delivered through microcatheters such as the type disclosed in U.S. Pat. No. 4,739,768, to Engelson. The microcatheter commonly tracks a guide wire to a point just proximal of or within the desired site for occlusion. After removal of the guide wire, the coil is advanced through the microcatheter and out the distal end hole so to at least partially fill the selected space and create an occlusion.

Once a vaso-occlusion coil is implanted at a desired site, occlusion results either from the space-filling mechanism inherent in the coil itself, or from a cellular response to the coil such as a thrombus formation, or both. The space-filling mechanism of the vaso-occlusion coil may be either based upon a predetermined secondary geometry, or may be based upon random flow characteristics of the coil as it is expelled from a delivery sheath lumen.

Various commercially available vaso-occlusion coils have a secondary shape which dictates (at least in part) a space-filling occlusion mechanism. Such a secondary shape may include a secondary helical structure which involves the primary coil helix being itself wound into a second helix. In addition to the space-filling feature, another benefit to having a secondary coil shape is that it may allow the coil readily to anchor itself against the walls of a delivery site. For example, a vaso-occlusion coil having a secondary shape may be ejected from a sheath lumen where it was constrained in a stretched condition to have a first outer diameter equal to the sheath lumen inner diameter. When ejected, the coil passively expands to its secondary shape, often having a larger, second outer diameter to aid in space-filling the body cavity or lumen. This may be an expansion to the coil's relaxed, unrestrained memory state—or at least until the coil encounters a vessel wall against which it exerts a force to complete the anchoring process.

One example of a type of vaso-occlusion coil having a pre-determined secondary shape is described in U.S. Pat. No. 4,994,069, to Ritchart et al. Ritchart et al describes a vaso-occlusive wire having a memory imparted thereto by heating the wire at about 800° F. for 24 hours after it is shaped. This memory is effective to return the wire from a stretched, linear condition (in which shape it is advanced through a catheter) to a space-filling relaxed condition as the wire is released from the catheter. The diameter of the secondary shape may be approximately equal to or even larger than the vessel in which it is deployed.

In addition to vaso-occlusion coils having pre-determined secondary shapes that dictate in part their space-filling mechanism, other vaso-occlusion coils have been disclosed that take on random shapes when expelled from a delivery catheter. One such type of vaso-occlusive coil is often referred to as the "liquid coil." An example of such a vaso-occlusive coil which takes on a random occlusive shape when delivered into a body space is shown in U.S. Pat. No. 5,718,711, issued Feb. 17, 1998, to Berenstein et al. This patent describes very soft, flexible coils which are flow-injectable through the delivery catheter using, e.g., a saline solution.

In addition to the various types of space-filling mechanisms and geometries of vaso-occlusion coils, other particularized features of coil designs, such as mechanisms for delivering vaso-occlusion coils through delivery catheters and implanting them in a desired occlusion site, have also been described. Examples of categories of vaso-occlusion coils based upon their delivery mechanisms include pushable coils, mechanically detachable coils, and electrolytically detachable coils.

One example of the type of vaso-occlusion coil referred to as the "pushable coil" is disclosed in U.S. Pat. No. 4,994,069 to Ritchart et al., introduced above. Pushable coils are commonly provided in a cartridge and are pushed or "plunged" from the cartridge into a delivery catheter lumen. A pusher rod advances the pushable coil through and out of the delivery catheter lumen and into the site for occlusion.

In contrast to pushable coils, mechanically detachable vaso-occlusion coils are integrated with a pusher rod and mechanically detached from the pusher after exiting a delivery catheter. Examples of such mechanically detachable vaso-occlusion coils are provided in U.S. Pat. No. 5,261,916 to Engelson, or U.S. Pat. No. 5,250,071 to Palermo.

Further in contrast to the mechanically detachable type of vaso-occlusion coil, the electrolytically detachable type is also integrated with a pusher rod, but is detached from the pusher by applying a direct current that dissolves a sacrificial link between the pusher and the coil. Examples of such electrolytically detachable vaso-occlusion coils are disclosed in U.S. Pat. No. 5,122,136 to Guglielmi et al, and U.S. Pat. No. 5,354,295 also to Guglielmi, et al.

Improvements for enhancing the thrombogenic or other occlusive tissue response to metal coils have also been disclosed. For example, vaso-occlusion coils having vaso-occlusive fibers attached thereto have been described (see for example, U.S. Pat. No. 5,226,911 to Chee et al.).

Vaso-Occlusion Coils in Aneurysms

A wide variety of clinical abnormalities in body lumens may be treated with artificial occlusion methods. For example, artificial occlusion methods have been disclosed for treating feeder vessels into tumors, arterio-venous malformations, fistulas, and aneurysms of vessel walls. Among arterial abnormalities, aneurysms present particular medical risk due to the dangers of potential rupture of the thinned wall inherent in an aneurysm. Occlusion of aneurysms with vaso-occlusion coils without occluding the adjacent artery is a desirable method of reducing such risk.

In one disclosed method of treating aneurysms with vaso-occlusion coils, a microcatheter is initially steered into or adjacent the entrance of an aneurysm, aided by a steerable wire. The wire is then withdrawn from the microcatheter lumen and replaced by the vaso-occlusion coil. The vaso-occlusion coil is advanced through and out of the microcatheter, desirably being completely delivered into the aneurysm. After or during delivery of such a coil into the aneurysm, a portion of the coil might then migrate out of the aneurysm entrance zone and into the feeding vessel. This may cause an undesirable response of occluding the feeding vessel. Also, there is an additional risk that the blood flow may induce movement of the coil farther out of the aneurysm, resulting in a more developed embolus in the good vessel.

One type of aneurysm, commonly referred to as a "wide-neck aneurysm," is known to present particular difficulty in placing and retaining vaso-occlusion coils. Wide-neck aneurysms are herein referred to as aneurysms of vessel walls having a neck or "entrance zone" from the adjacent vessel, which entrance zone has a diameter that either: (1) is at least 80% of the largest diameter of the aneurysm; or (2) is clinically observed to be too wide to effectively retain vaso-occlusion coils that are deployed using conventional techniques.

In attempting to prevent potential migration of vaso-occlusion coils from aneurysms, catheter distal tip shapes may be formed on delivery microcatheters to help support the distal tip during deployment of vaso-occlusive agents. However, this may provide only a partial solution, particularly in the case of wide-neck aneurysms. There is a need for a retaining device that a.) at least partially blocks an entrance zone to an aneurysm so that occlusion devices may be implanted in and retained within the aneurysm and are prevented from migrating through the entrance zone of the aneurysm and into the adjacent vessel, and b.) is at least partially coated with or associated with a composition causing an angiogenic response so to promote at least partial closing of the entrance to the aneurysm.

SUMMARY OF THE INVENTION

This invention is an implantable medical device assembly for use in surgical procedures. It is most preferably an implantable structure, perhaps having stenting properties, but that is only partially coated with a material having angiogenic properties or is partially associated with a material, e.g., a mesh or the like causing a localized angiogenic response. One variation of the invention is an artificial occlusion kit having the inventive implantable stenting structure and vaso-occlusive devices. The inventive implantable stenting structure is typically situated so to prevent migration of artificial occlusion devices or implants from an occlusion site, such as an aneurysm, and into an adjacent body space, such as a blood vessel. This invention includes a related method of use.

The inventive artificial occlusion kit is for the implantation and retention of an artificial occlusion device in a body space adjacent to and extending from a body lumen in a mammal. The artificial occlusion kit has at least one occlusion device suitable for filling at least a portion of the body space and a retaining device assembly at least partially coated with a material having angiogenic properties.

The retaining device of the artificial occlusion kit typically may be delivered and implanted at a retaining site in the body lumen adjacent to the body space to be occluded. Usually, this retaining device has a first shape that is radially expandable to a diameter that is sufficient to engage the wall of the body lumen at a retaining site adjacent the body space to be occluded. When engaged with the body lumen wall, the retaining device forms a lumen having a diameter that is sufficient to allow flow through that lumen, and also forms a barrier that prevents occlusion devices that are implanted in the body space from migrating out of the body space and into the adjacent body lumen. The inventive retaining device is either (or both) partially coated with a composition or associated with a composition or covering causing a localized angiogenic response. The angiogenic composition or covering is placed on the inventive retaining device at least in the region of the mouth of the aneurysm, generally in a quiescent region. This permits the angiogenic composition or covering to accelerate the formation of blood vessels in the mouth of the aneurysm and enhance the closure of the aneurysm.

In one retaining device variation, the expanded shape is a mesh or braid having the angiogenic composition or covering only exterior to the retaining device and only on, e.g., a portion of the circumference of the exterior of the device or a portion of the length of the device or with both of these configurations. The inventive retaining device may be self-expanding to a second shape with an expanded outer diameter upon delivery to the retaining site upon release at the retaining site. Alternatively, the retaining device may be balloon expandable from the first shape to the second or deployed shape.

In another variation of the invention, the retaining device may be a metal wire wound into a primary helix that has a secondary geometry which is also a secondary helix. This variation of the retaining device similarly includes the angiogenic composition or covering only exterior to the retaining device as deployed and only on, e.g., a portion of the circumference of the exterior of the device or a portion of the length of the device or with both of these coating configurations.

This invention includes methods for using the apparatus here described.

BRIEF DESCRIPTION OF THE DRAWINGS

FIG. 1A shows a partial side view of a retaining device made according to the invention.

FIG. 1B shows a cross-sectional end view of the retaining device of FIG. 1A.

FIG. 2A shows a partial side view of a retaining device made according to the invention.

FIG. 2B shows a cross-sectional end view of the retaining device of FIG. 2A.

DESCRIPTION OF THE INVENTION

This invention provides a solution to the dual problems of a.) vaso-occlusion device migration out of aneurysms or other implantation sites and into the feeding vessels that are not the target of vaso-occlusion, and b.) longer term closure of the mouth of the aneurysm by the growth of blood vessels at the mouth of the aneurysm. An inventive retaining device having a composition or covering causing an angiogenic response and only exterior to the retaining device as deployed and only on, e.g., a portion of the circumference of the exterior of the device or a portion of the exterior of the length of the device or with both of these coating configurations is used in a novel artificial occlusion assembly to prevent migration of one or more occlusion devices from a target occlusion site by forming a short term barrier at the entrance zone to the target site from a feeding vessel and to provide a longer term barrier via promotion of the growth of blood vessels at the mouth of the aneurysm.

Implantable Stenting Structure Partially Coated with an Angiogenic Causing Material FIGS. 1A, 1B, 2A, 2B, and 3 show a number of variations of the inventive implantable stenting structure.

FIGS. 1A and 1B show a first variation of the inventive implantable stenting structure (100). The variation is a helically wound coil made up of a number of helically wound turns (104) which are partially coated with an angiogenic coating (106). The angiogenic coating (106) is only on the exterior of the inventive implantable stenting structure (100). In this variation, the angiogenic coating (106) is present on the portion of the circumference (shown in FIG. 1B) which will ultimately be nearest the aneurysm mouth. The angiogenic coating (106) is present only on a portion of the circumference. It should be understood that when the inventive structure (100) is placed in the delivery catheter (as is depicted in FIGS. 4A–4E below), the angiogenic coating (106) is present on the wire apparently at a series of unconnected areas.

Figure 3:
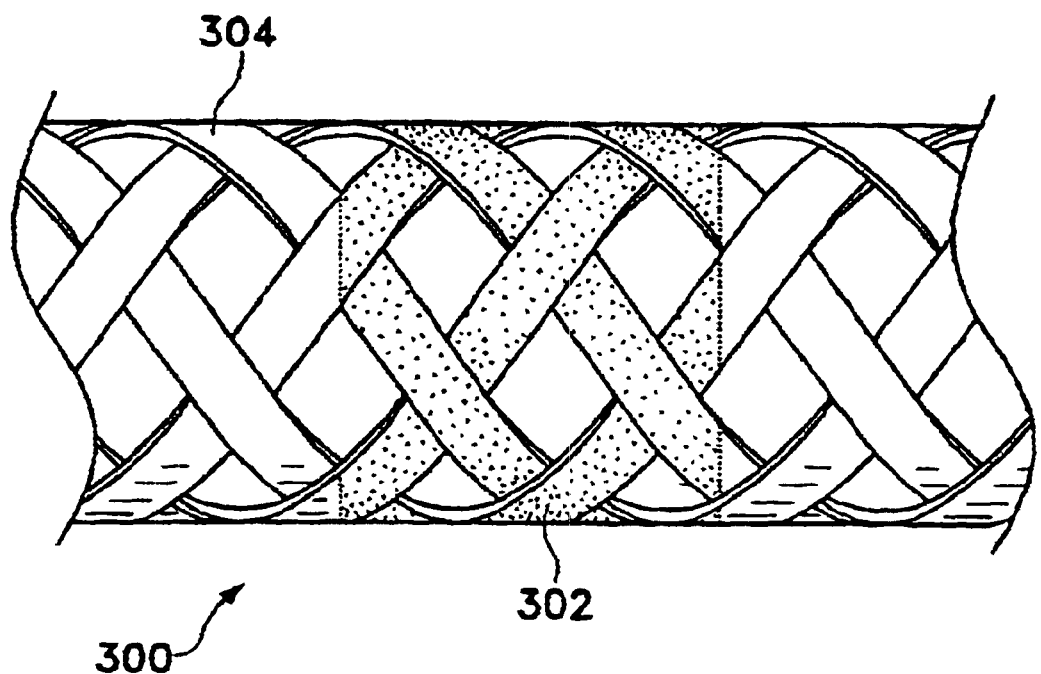
FIG. 3 shows a partial side view of a retaining device made according to the invention.

It is within the scope of the invention that the angiogenic coating (106) is placed along only a portion of the longitudinal axis of the implantable stenting structure (100) much in the way as that shown in FIG. 3.

FIGS. 2A and 2B show respectively a side view and a cross-section of a second variation of the inventive implantable stenting structure (200). The generalized structure is an expandable stent (self-expanding or balloon-expandable) as is known in the art having an angiogenic coating (206) which is present only on a portion of the outer surface. FIGS. 2A and 2B show the variation in which a portion of the circumference of the inventive implantable stenting structure (200) is coated with an angiogenic coating (206). Again, the stent itself (204) is at least partially covered with the angiogenic coating (206) and, in this case the circumference is covered with perhaps 180° of the angiogenic coating (206). The length of the arcuate covering is not especially critical but should be chosen to overlap the mouth of the aneurysm, when deployed.

FIG. 3 shows a further variation of the inventive implantable stenting structure (200) having a partial exterior coating of the angiogenic material (302). In this instance, the angiogenic coating (302), although only on the exterior of the stenting device (304), also is found only on a portion of the axial length of the stenting device (304).

Figure 4:
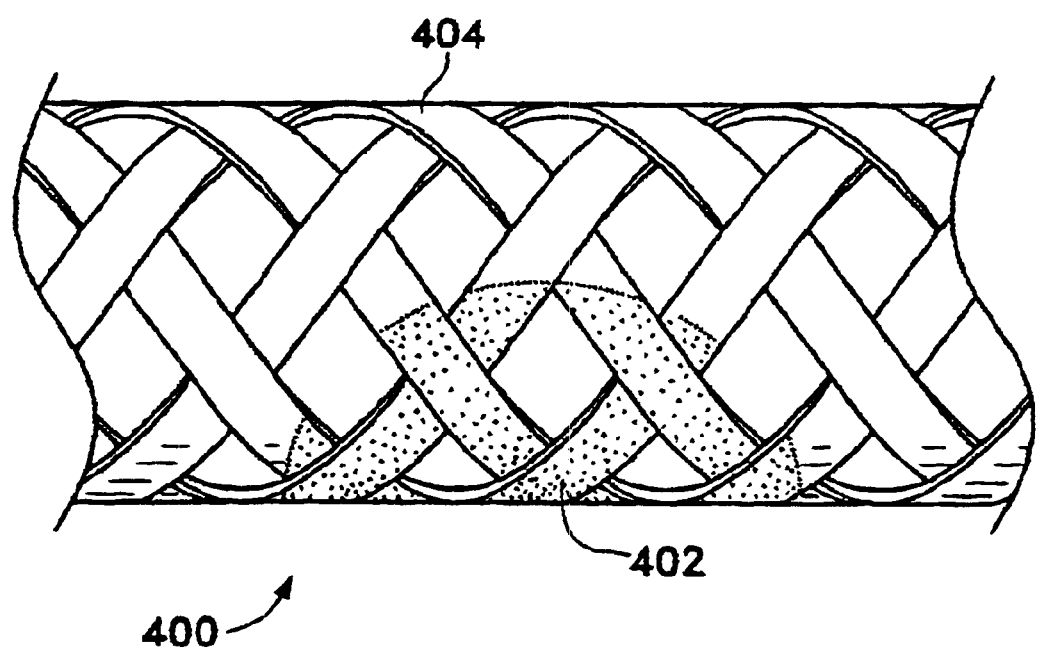
FIG. 4 shows a partial side view of a retaining device made according to the invention.

Finally, FIG. 4 shows a variation of the inventive implantable stenting structure (300) having a partial exterior coating of the angiogenic material (402). In this instance, the angiogenic coating (402), again is only on the exterior of the stenting device (404), is found on a portion of the exterior of the stenting device (404) in a region generally mimicking the mouth of the aneurysm to which it will be applied; the coating of the angiogenic material (402) is limited in length of the axial length of the stenting device (304) and the portion of the circumference of the inventive implantable stenting structure (304).

Additionally, the exterior region of the inventive implantable stenting structures as shown and discussed above in conjunction with FIGS. 1A–4 may also be "associated" with a composition or covering causing a localized angiogenic response. By "associated" is meant that the material is tied to or is made to adhere to the stenting structure. The composition may be a fabric or gauze-like structure. It may also be a non-woven or loose agglomeration of individual fibers. In general, they need to stay in place during the placement of the device in the body.

Preferably, the associated covering or composition is a polymeric material such as a biodegradable polymer, e.g., polyglycolic acid, polylactic acid, reconstituted collagen, poly-p-dioxanone, and their copolymers such as poly(glycolide-lactide) copolymer, poly(glycolide-trimethylene carbonate) copolymer, poly(glycolide-$\epsilon$-caprolactone) copolymer, glycolide-trimethylene carbonate triblock copolymer, and the like. Mixtures of the noted polymers, e.g., of polylactide and polyglycolide may also be used. The associated coverings may also be used in conjunction with the bioactive coatings discussed above.

As will be discussed below, this inventive implantable stenting structure preferably is sized so that when deployed, it does not exert significant pressure against the vessel wall. Although it should be large enough in diameter that it stays in position against the mouth of the aneurysm, it should not appreciably deform the vessel. The aneurysm is almost always fragile and the retainer should not be a potential source of harm.

Each of the structures noted just above may be produced using materials that are biocompatible and preferably either metallic or polymeric. Appropriate materials for these inventive devices, when self-deploying, include alloys such as super-elastic alloys. Super-elastic or pseudoelastic shape recovery alloys are well known in this art. For instance, U.S. Pat. Nos. 3,174,851; 3,351,463; and 3,753,700 each describe one of the more well known super-elastic alloys, known as Nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its super-elastic properties. The alloy mentioned in the three patents just above, is a nickel titanium alloy. It is readily commercially available and undergoes the austenitic-SIM-austenitic transformation at a variety of temperatures between −20° C. and +30° C.

These alloys are especially suitable because of their capacity to recover elastically, almost completely, to the initial configuration once the stress is removed. Typically in services such as are described here there is little permanent plastic deformation, even at relatively high strains. This ability allows the retainer device to undertake substantial bends both as it is collapsed to enter the various tubular delivery devices and as it undertakes further bending in passing through the vasculature. In spite of this bending, it returns to its original shape once the bend has been traversed without retaining kinks or permanent bends.

Of the super-elastic alloys currently available, we consider our preferred material to be nominally 50.6±2% nickel with most of the remainder being titanium. Up to about 5% of the alloy may be a member of the iron group of metals, particularly chromium and iron. The alloy should not contain more than about 500 parts per million of oxygen, carbon, or nitrogen. The transition temperature of this material is not particularly important, but it should be reasonably below the typical temperature of the human body so to allow it to be in its austenitic phase during use. The diameter of the wires or ribbons making up the various array elements preferably are smaller than about 0.010 inches in diameter. These super-elastic alloys are not always completely visible under fluoroscopy as it is used in the human body. Consequently it may be desirable to add a covering of some kind to improve the radio-opacity of the device. Radio-opaque metals such as gold and platinum are well known. They may be added the various elements of this inventive device by such widely recognized methods as by plating or by wrapping the element in a radio-opaque wire or ribbon.

Although we have discussed producing these devices from super-elastic alloys, other metals may in certain circumstances be appropriate. Such metals include a number of the stainless steels and other highly elastic, if not super-elastic alloys.

The inventive stenting device may be made of much more inelastic, but malleable materials, such as tantalum, titanium, silver, gold, platinum, and alloys of these materials when the stent is to be expanded and deployed using, e.g., a balloon.

Furthermore, it is within the scope of this invention that the various elements be of polymeric materials. Polymeric materials are somewhat easier to work with in forming a device. Such polymeric materials are well known in this art and may include members from the group of polyethylene, polypropylene, polytetrafluoroethylene, various Nylons, and the like. These polymers are easily chosen by one having ordinary skill in this art for the purposes shown here.

Angiogenic Material

Non-limiting examples of angiogenic materials which increase cell attachment and/or thrombogenicity include both natural and synthetic compounds, e.g., collagen, fibrinogen, vitronectin, other plasma proteins, growth factors (e.g., vascular endothelial growth factor, "VEGF"), synthetic peptides of these and other proteins having attached RGD (arginine-glycine-aspartic acid) residues, generally at one or both termini, or other cell adhesion peptides, i.e., GRGDY, oligonucleotides, full or partial DNA constructs, natural or synthetic phospholipids, or polymers with phosphorylcholine functionality. In addition, polynucleotide sequences encoding peptides (e.g., genes) involved in wound healing or promoting cellular attachment may also be used. Other components having a specific role may be included, e.g., genes, growth factors, biomolecules, peptides, oligonucleotides, members of the integrin family, RGD-containing sequences, oligopeptides, e.g., fibronectin, laminin, bitronectin, hyaluronic acid, silk-elastin, elastin, fibrinogen, and other basement membrane proteins with bioactive agents.

Other bioactive materials which may be used in the present invention include, for example, pharmaceutically active compounds, proteins, oligonucleotides, ribozymes, anti-sense genes, DNA, cDNA or RNA compacting agents, gene/vector systems (i.e., anything that allows for the uptake and expression of nucleic acids), nucleic acids (including, for example, naked DNA, cDNA, RNA, and DNA, cDNA or RNA in a non-infectious vector or in a viral vector which may have attached peptide targeting sequences; antisense nucleic acids (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like. For example, biologically active solutes include anti-thrombogenic agents such as heparin, heparin derivatives, urokinase, PPACK (dextrophenylalanine proline arginine chloromethylketone), rapamycin, probucol, and verapimil; anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/ antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine, anti-coagulants such as D-Phe-Pro-Mg choloromethyl ketone, an RGD peptide-containing compound, antithrombin compounds, platelet receptor antagonists, anti-thrombin antibodies, anti-platelet receptor antibodies, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bufunctional molecules consisting of an antibody and a cytotoxin; cholestrol-lowering agents; vasodilating agents; agents which interfere with endogenous vasoactive mechanisms, and combinations thereof. These and other compounds are applied to the stenting device.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation production of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated into the polymer coating 130, or whose DNA can be incorporated, include without limitation, proteins competent to induce angiogenesis, including factors such as, without limitation, acidic and basic fibroblast growth factors, vascular endothelial growth factor (including VEGF-2, VEGF-3, VEGF-A, VEGF-B, VEGF-C) hif-1 and other molecules competent to induce an upstream or downstream effect of an angiogenic factor; epidermal growth factor, transforming growth factor α and β, platelet-derived endothelial growth factor, platelet-derived growth factor, tumor necrosis factor a, hepatocyte growth factor and insulin like growth factor; growth factors; cell cycle inhibitors including CDK inhibitors; thymidine kinase ("TK") and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

In one exemplary embodiment of the present invention, the medical device has recombinant nucleic acid incorporated therein, wherein the recombinant nucleic acid comprises a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u."), preferably at least about $10^{11}$ p.f.u. Alternatively, the concentration of the viral vector is limited by the concentration that results in an undesirable immune response from a patient.

The angiogenic materials or bioactive agents may further contain additional materials which have one or more functions, including, but not limited to, providing a therapeutic for local or blood borne delivery, or enhancing thrombosis, coagulation, or platelet activity.

Artificial Occlusion Kit with Retaining Device

The kit of this invention is made up of the inventive implantable stenting structure and one or more vaso-occlusive devices. Preferred vaso-occlusive devices are helically wound coils having a secondary shape as may be found in, e.g., U.S. Pat. No. 5,853,418, to Ken et al, perhaps with a stretch-resisting member. The kit may also include the catheter which delivers the retaining device to the selected body site.

The preferred vaso-occlusive device is a helically wound coil produced from one or more wires. This simple helical form is referred to as the "primary" winding or shape. As is known in the art, the primary form often includes a stretch-resisting member which is fixedly attached to both ends of the coil and is located in the lumen of the coil. The stretch-resisting member is typically fibrous and desirably polymeric. It may be thermoplastic or thermosetting and comprise a bundle of threads or a single filament melted onto, glued, or otherwise fixedly attached to the vaso-occlusive coil.

The materials used in constructing the vaso-occlusive coil and the stretch resisting member may be any of a wide variety of materials; preferably, a radio-opaque material such as a metal or a polymer is used. Suitable metals and alloys for the wire making up the primary coil and the stretch-resisting member include the Platinum Group metals, especially platinum, rhodium, palladium, rhenium, as well as tungsten, gold, silver, tantalum, and alloys of these metals. These metals have significant radio-opacity and in their alloys may be tailored to accomplish an appropriate blend of flexibility and stiffness. They are also largely biologically inert. Highly preferred is a platinum/tungsten alloy, e.g., 8% tungsten and the remainder platinum.

The coils and stretch-resisting members may also be of any of a wide variety of stainless steels and super-elastic alloys if some sacrifice of radio-opacity and flexibility may be tolerated.

The coils may be made of radiolucent fibers or polymers (or metallic threads coated with radiolucent or radio-opaque fibers) such as Dacron (polyester), polyglycolic acid, polylactic acid, fluoropolymers (polytetrafluoro-ethylene), Nylon (polyamide), or even silk. Should a polymer be used as the major component of the vaso-occlusive coil member, it is desirably filled with some amount of a radio-opaque material such as powdered tantalum, powdered tungsten, bismuth oxide, barium sulfate, and the like.

As noted above, the coil material is generally first wound into a primary coil. The primary coil is typically linear after it has been wound. Generally speaking, when the coil is a metallic coil and that coil is a platinum alloy or a super-elastic alloy such as nitinol, the diameter of the wire used in the production of the coil will be in the range of 0.00025 and 0.006 inches. The wire is wound into a primary coil having a primary diameter of between 0.003 and 0.025 inches. For most neurovascular indications, the preferable primary coil diameter is 0.008 to 0.018 inches. We have generally found that the coil wire may be of sufficient diameter to provide a hoop strength to the resulting device sufficient to hold the device in place within the chosen body site, lumen or cavity, without substantially distending the wall of the site and without moving from the site as a result of the repetitive fluid pulsing found in the vascular system.

The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the invention. However, only dimensions suitable for use in occluding sites within the human body are included in the scope of this invention.

Suitable polymeric materials for the polymeric stretch-resisting member are either thermosetting or thermoplastic. Thermoplastics are preferred because they allow simplification of the procedure for constructing the device since they may be melted and formed into the coil ends. Suitable polymers include most biocompatible materials which may be made into fibers but include polyester such as polyethyleneterephthalate (especially Dacron) and polyamides including the Nylons, polyglycolic acid, polylactic acid, fluoropolymers (polytetrafluoro-ethylene), or even silk. Especially preferred because of the long history of safe and effective usage in the human body is fibrous polyethylene-terephthalate (PET) sold as Dacron.

As was noted above, the desired helically wound vaso-occlusive devices may have a simple linear shape or may have shapes which are not so simple. Many patents show what are termed "secondary" shapes in that they are formed from the primary coil by the simple act of winding the primary coil on a form of a desired shape and then heat treating the so-formed shape. Secondary shapes go from the simple "C" shaped coil assembly to complicated generally spherical shapes. Any secondary shape shown in the art is suitable for this invention.

Additionally, these vaso-occlusive devices may also be used in conjunction with various external fiber adjuncts. The filamentary material may loop through the coil as described in U.S. Pat. Nos. 5,226,911 and 5,304,194, to Chee et al. The filamentary material may be a braided covering enveloping a coil such is described in U.S. Pat. No. 5,382,259, to Phelps et al.

The fibrous materials may be made from a biocompatible materials such as Dacron (polyester), polyglycolic acid, polylactic acid, fluoropolymers (polytetrafluoroethylene), Nylon (polyamide), or silk. The materials mentioned, to the extent that they are thermoplastics, may be melted or fused to the coils. Alternatively, they may be glued or otherwise fastened to the coils. Preferred materials are Dacron.

Deployment of the Retaining Device

FIGS. 5A–E show sequential steps for occluding a body space—here an aneurysm of a body lumen wall—using the artificial occlusion kit embodiment of this invention. In this series of Figures, a retaining device is provided in a kit together with at least one vaso-occlusion device, which kit is also shown in use with at least one delivery catheter.

Figure 5A:
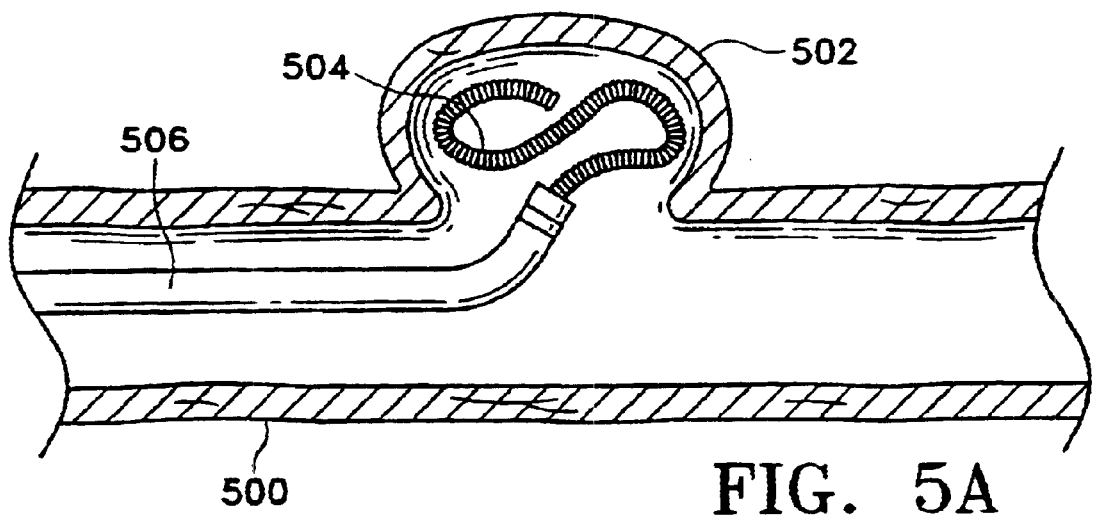
FIGS. 5A–5E show a procedure for deploying the devices and kits of the invention.
Figure 5B:
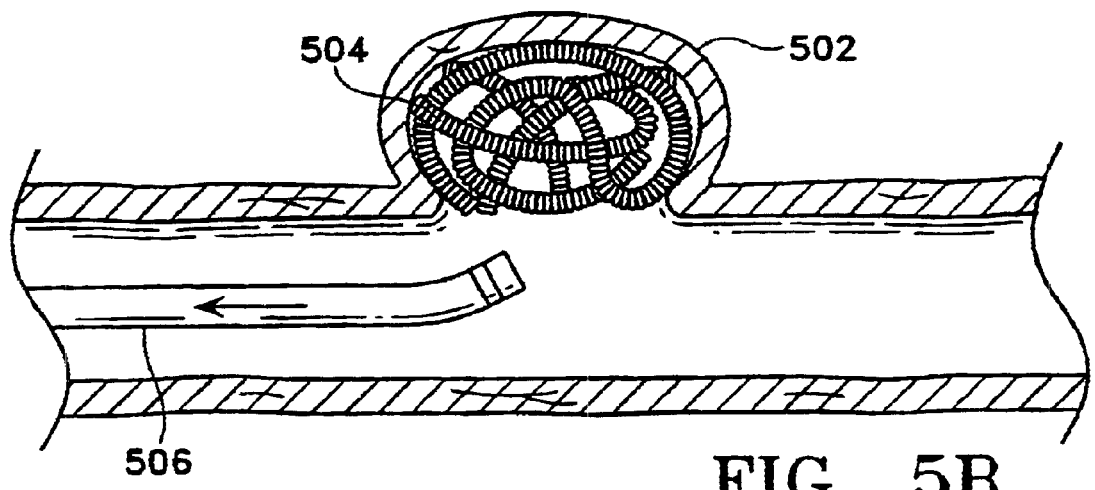
Figure 5C:
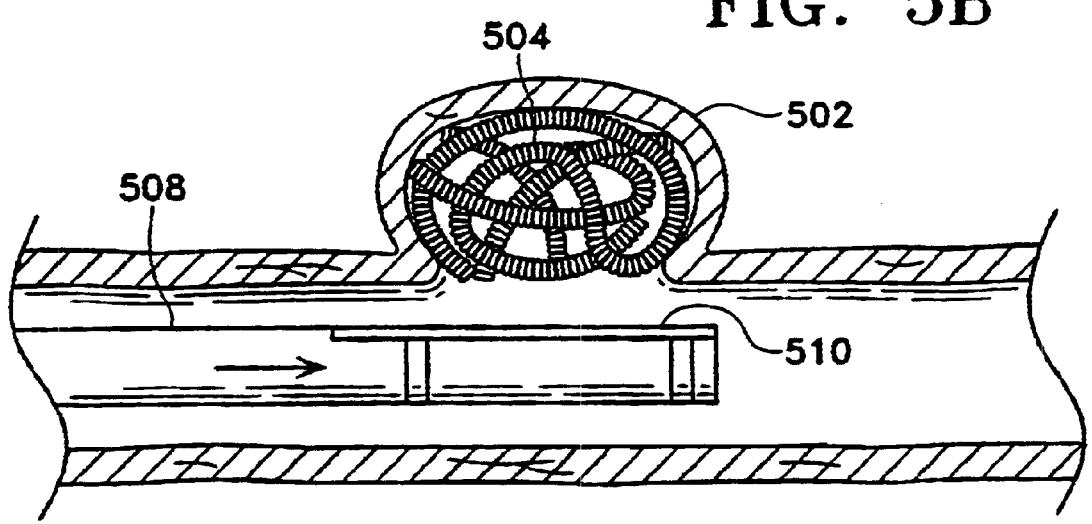
Figure 5D:
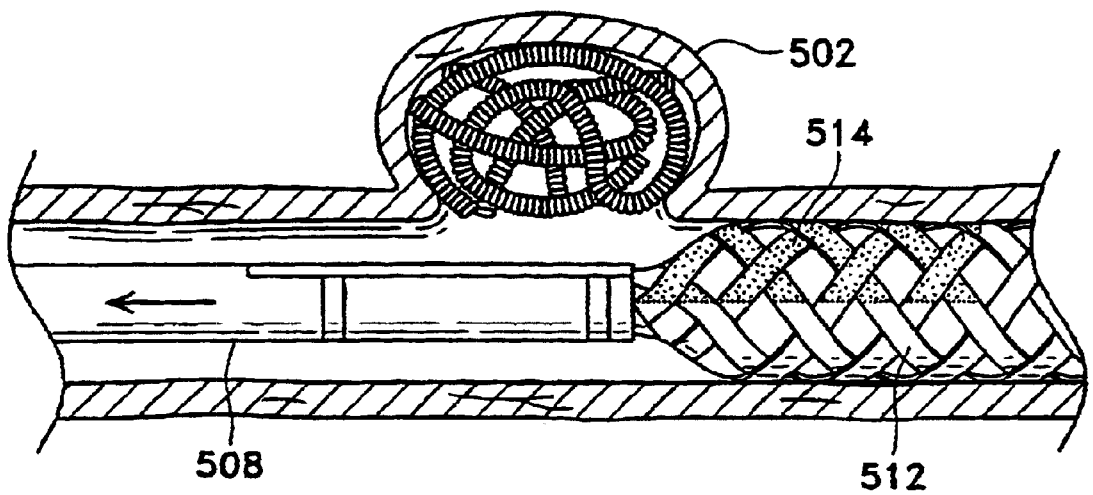
Figure 5E:
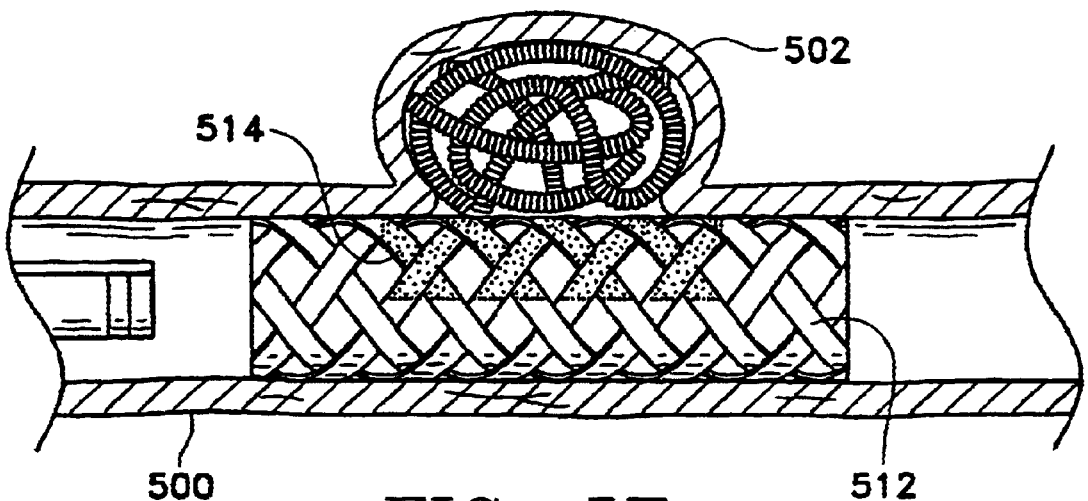

FIG. 5A shows one or more vaso-occlusion coils being implanted into an aneurysm. In FIG. 5B, the vaso-occlusive coil delivery catheter is being with drawn. In FIG. 5C, a retaining device delivery catheter is sited at the aneurysm. In FIG. 5D, the retaining device is shown being delivered to a retaining site in the body lumen adjacent the aneurysm after the aneurysm is at least partially occluded with vaso-occlusion coils. In FIG. 5E, the retaining device is completely implanted at the retaining site. The implanted retaining device shown forms a barrier against migration of the vaso-occlusion coils from the aneurysm and into the body lumen, while maintaining an open conduit for flow through the body lumen. It also is situated so that the angiogenic material is in the general area of the mouth of the aneurysm.

In FIG. 5A, a cut-away side view of a vessel (500) having an aneurysm (502) in its wall is shown. Vaso-occlusion coil (504) is shown being delivered into aneurysm (502) out of the distal end of delivery catheter (506) in order to occlude the aneurysm (502).

Vaso-occlusion coil (504) for the purposes of this invention may be any one of a wide variety of coils that were discussed above and are known in the art for occluding vessels or aneurysms.

The appropriate design for delivery catheter (506) is defined by the ability to reach the desired occlusion site atraumatically and to efficaciously deliver the vaso-occlusion coil into the site as an occlusion implant. One example of a catheter that may be used in the present invention is described in U.S. Pat. No. 4,739,768 to Engelson.

FIG. 5B shows the step of removing the vaso-occlusion coil delivery catheter (506) after completion of the step of filling the aneurysm (502) with vaso-occlusion coils (504).

FIG. 5C shows the step of introducing a retaining device delivery catheter (508) into the region near the aneurysm (502). The retaining device delivery catheter (508) need not be a different catheter than that used to introduce the vaso-occlusion coils (504), but may be if the size of the retaining device is quite large in comparison to the vaso-occlusion coils (504). In any case, it is usually desirable to place the tip of the retaining device delivery catheter (508) past the mouth of the aneurysm (502) for proper placement of the retaining device. Additionally, in some variations of the invention, specifically those in which the retaining device has angiogenic material on only one portion of the circumference of the retaining device, the catheter should have a longitudinal radio-opaque marker (510) which allows the user to position the catheter in alignment with the aneurysm so that the angiogenic material on the retaining device faces and is contiguous with the mouth of the aneurysm (502).

FIG. 5D shows a retaining device (512) having angiogenic material (514) being delivered through delivery catheter (508) and into vessel (500) at the site of aneurysm (502). A plurality of vaso-occlusion coils may be implanted into aneurysm (502) prior to delivery of the retaining device (512). In this instance, the retaining device (512) having angiogenic material (514) is a self-expanding device which is pushed out of the delivery catheter (508).

As noted above, it is highly desirable to select a retaining device (512) having a size and hoop stress which does not place significant stress on the wall of the vessel (500) while still both staying in position in the vessel (500) and retaining the vaso-occlusion coils (504) within aneurysm (502). Note that the angiogenic material (514) is situated against the mouth of aneurysm (502).

Alternatively, a further retaining device variation may be delivered upon and expanded by a balloon on the distal end of a balloon catheter. In such a variation, the retaining device is provided for delivery to the retaining site while it is formed in its first shape coaxially engaged over a balloon in a deflated state. Once at the retaining site, inflation of the balloon radially expands the retaining device into a second shape having an outer diameter sufficient to engage the vessel wall and which forms a barrier across the entrance zone to an aneurysm. Subsequent deflation and withdrawal of the balloon leaves the radially expanded retaining device implanted at the retaining site, which retaining device forms a lumen where the expanded balloon once was.

FIG. 5E shows the retaining device (512) having angiogenic material (514) in place at the site of aneurysm (502). Delivery catheter (508) is in the process of being withdrawn from vessel (500). The angiogenic material (514) is against the mouth of the aneurysm (502).

Modification of the above-described variations for carrying out the invention that would be apparent to those of skill in the fields of medical device design are intended to be within the scope of the following claims.

We claim as our invention:

1. An artificial occlusion kit for retaining an artificial occlusion device in a body space to be occluded adjacent to and extending from a body lumen in a mammal, comprising:
    at least one occlusion device for filling at least a portion of the body space; and
    a retaining device deliverable and implantable at a retaining site in the body lumen adjacent to the body space, said retaining device having two opposite ends and forming a first shape with a first outer diameter, said retaining device being expandable to a second shape having a second outer diameter larger than said first outer diameter and sufficient to engage a body lumen wall at the retaining site such that a barrier is formed against migration of said at least one occlusion device out of the body space and into the body lumen, said second shape being only partially coated or associated with at least one material effective to cause a localized angiogenic response, said second shape also forming a lumen along a longitudinal axis sufficient to allow flow of fluids therethrough.

2. The artificial occlusion kit of claim 1 wherein said retaining device forms said first shape when constrained for delivery to the retaining site, and forms said second shape upon release from said constraint at the retaining site.

3. The artificial occlusion kit of claim 2 further comprising:
    a delivery catheter having a proximal delivery catheter end with a proximal delivery port, an opposite distal delivery catheter end portion with a distal delivery port, and a delivery lumen extending between said delivery ports and having a delivery lumen inner diameter less than said second outer diameter, wherein said retaining device is slidably disposable under constraint within said delivery lumen.

4. The artificial occlusion kit of claim 1 wherein said at least one occlusion device for filling at least a portion of the body space comprises one or more helically wound coils.

5. The artificial occlusion kit of claim 1 wherein said at least one material effective to cause a localized angiogenic response comprises at least one material which increases cell attachment or thrombogenicity.

6. The artificial occlusion kit of claim 5 wherein said at least one material which increases cell attachment or thrombogenicity is selected from the group consisting of collagen, fibrinogen, vitronectin, other plasma proteins, growth factors synthetic peptides of these and other proteins having attached RGD (arginine-glycine-aspartic acid) residues (at one or both termini), and cell adhesion peptides.

7. The artificial occlusion kit of claim 1 wherein said at least one material which increases cell attachment or thrombogenicity is selected from the group consisting of GRGDY, oligonucleotides, full or partial DNA constructs, natural or synthetic phospholipids, and polymers with phosphorylchlorine functionality.

8. The artificial occlusion kit of claim 1 wherein said at least one material effective to cause a localized angiogenic response comprises at least one material having a polynucleotide sequence encoding a peptide involved in wound healing or promoting cellular attachment.

9. The artificial occlusion kit of claim 1 wherein said at least one material effective to cause a localized angiogenic response further comprises at least one component having a specific role selected form the group consisting of genes, growth factors, biomolecules, peptides, oligonucletides, members of the integrin family, RGD-containing sequences, and oligopeptides.

10. The artificial occlusion kit of claim 9 wherein said at least one component having a specific role comprises at least one oligopeptide selected from the group consisting of fibronectin, laminin, vitronectin, hyaluronic acid, acid-elastin, elastin, fibrinogen, and other basement membrane proteins with bioactive activity.

11. The artificial occlusion kit of claim 1 wherein said at least one material further comprises at least one component having one or more functions, including, but not limited to, providing a therapeutic for local or blood borne delivery, or enhancing thrombosis, coagulation, or platelet activity.

12. The artificial occlusion kit of claim 1 wherein said at least one material effective to cause a localized angiogenic response comprises one or more polymers.

13. The artificial occlusion kit of claim 12 wherein said one or more polymers is selected from the group consisting of polyglycolic acid, polylactic acid, reconstituted collagen, poly-p-dioxanone, and their copolymers such as poly (glycolide-lactide) copolymer, poly(glycolide-trimethylene carbonate) copolymer, poly(glycolide-ε-caprolactone) copolymer, glycolide-trimethylene carbonate triblock copolymer, and mixtures.

14. An artificial occlusion kit for occluding a body space adjacent to and extending from a body lumen, the kit comprising:
   at least one occlusion device for filling at least a portion of the body space; and
   a retaining device deliverable and implantable at a retaining site in the body lumen adjacent to the body space to retain the at least one occlusion device within the body space, the retaining device comprising:
     an expandable structure having a first, non-deployed shape and a second, deployed shape,
     wherein the retaining device expands from the first shape to the second shape after delivery to the retaining site to engage a body lumen wall at the retaining site,
     the expandable structure has uniform permeability when in the second shape, and
     the second shape forms a lumen along a longitudinal axis sufficient to allow flow of fluids therethrough; and
   a composition effective to cause a localized angiogenic response, wherein the first shape is coated or partially associated with the composition such that the second shape is only partially coated or partially associated with the composition.

15. The artificial occlusion kit of claim 14, wherein the second shape of the retaining device has an exterior surface and the composition only coats or is only associated with the exterior surface.

16. The artificial occlusion kit of claim 15, wherein the composition extends longitudinally along only a portion of the exterior surface of the retaining device.

17. The artificial occlusion kit of claim 16, wherein the composition extends circumferentially along only a portion of the exterior surface.

18. The artificial occlusion kit of claim 15, wherein the composition extends circumferentially along only a portion of the exterior surface.

19. The artificial occlusion kit of claim 14, the second shape is a mesh or a braid.

20. An artificial occlusion kit for occluding a body space adjacent to and extending from a body lumen, the kit comprising:
   at least one occlusion device for filling at least a portion of the body space; and
   a coil deliverable and implantable at a retaining site in the body lumen adjacent to the body space to retain the at least one occlusion device within the body space,
   the coil having a first, non-deployed shape and a second, deployed shape, wherein the coil expands from the first shape to the second shape after delivery to the retaining site, and
   the second shape being partially coated or associated with a composition effective to cause a localized angiogenic response.

21. A method of occluding a body space adjacent to and extending from a body lumen, comprising:
   implanting at least one occlusion device in the body space;
   delivering a retaining device to the body lumen adjacent to the body space in a first shape, the first shape being coated or associated with a composition effective to cause a localized angiogenic response;
   allowing the retaining device to expand from the first shape to a second shape to implant the retaining device in the body lumen, wherein the second shape comprises a structure having a uniform permeability, and the second shape is only partially coated or associated with the composition; and
   allowing fluid flow through the retaining device after implantation.

22. The method of claim 21, comprising:
   delivering the retaining device through a delivery catheter, wherein the retaining device is constrained in the first shape within the delivery catheter; and
   allowing the retaining device to expand by releasing the retaining device from constraint by pushing the restraining device out of the delivery catheter.

23. The method of claim 21, wherein the composition coats or is associated with only an exterior surface of the structure of the second shape of the retaining device.

24. The method of claim 23, wherein the composition coats or is associated with only a portion of the exterior surface.

25. The method of claim 24, wherein the composition extends only partially along the axial length of the exterior surface.

26. The method of claim 25, wherein the composition extends only partially around a circumference of the exterior surface.

27. The method of claim 24, wherein the composition extends only partially around a circumference of the exterior surface.

28. The method of claim 22, comprising positioning the retaining device such that the portion of the structure of the second shape coated or associated with the composition is adjacent to the body tissue around the body space.

29. The method of claim 25, wherein the body space is an aneurysm, the method comprising implanting the at least one occlusion device in the aneurysm.

30. An artificial occlusion kit for occluding a body space adjacent to and extending from a body lumen, the kit comprising:
   at least one occlusion device for filling at lest a portion of the body space; and
   a retaining device deliverable and implantable at a retaining site in the body lumen adjacent to the body space to retain the at least one occlusion device within the body space, the retaining device comprising:
   an expandible structure having a first, non-deployed shape and a second, deployed shape,
   wherein the retaining device expands from the first shape to the second shape after delivery to the retaining site to engage a body lumen wall at the retaining site,
   the expandible structure has uniform permeability when in the second shape, and
   the second shape forms a lumen along a longitudinal axis sufficient to allow flow of fluids therethrough; and
   a composition effective to cause a localized angiogenic response, wherein the first shape is coated or partially associated with the composition such that the second shape is only partially coated or partially associated with the composition.

* * * * *